(12) United States Patent
Samsoondar et al.

(10) Patent No.: US 6,917,422 B2
(45) Date of Patent: Jul. 12, 2005

(54) DEVICE FOR REFERENCE MEASUREMENT AND PHOTOMETRIC CORRECTION IN NON-INVASIVE GLUCOSE MEASUREMENT USING NEAR INFRARED SPECTROSCOPY

(75) Inventors: James Samsoondar, Cambridge (CA); Ashwani Kaushal, Mississauga (CA)

(73) Assignee: NIR Diagnostics Inc., Waterloo (CA)

( * ) Notice: Subject to any disclaimer, the term of this patent is extended or adjusted under 35 U.S.C. 154(b) by 98 days.

(21) Appl. No.: 10/348,342

(22) Filed: Jan. 22, 2003

(65) Prior Publication Data

US 2003/0174321 A1 Sep. 18, 2003

Related U.S. Application Data

(60) Provisional application No. 60/349,361, filed on Jan. 22, 2002.

(51) Int. Cl.[7] .................................................. G01J 1/10
(52) U.S. Cl. ..................................... 356/243.1; 356/300
(58) Field of Search ........................... 356/243.1, 243.2, 356/243.4, 243.5, 243.6, 243.7, 300; 600/322

(56) References Cited

U.S. PATENT DOCUMENTS

| 5,361,758 A | 11/1994 | Hall et al. |
| 5,429,128 A | 7/1995 | Cadell et al. |
| 5,596,450 A | 1/1997 | Hannon et al. |
| 6,015,610 A | 1/2000 | Minor et al. |

FOREIGN PATENT DOCUMENTS

WO        WO 01/15596 A1        3/2001

*Primary Examiner*—F. L. Evans
(74) *Attorney, Agent, or Firm*—Sterne, Kessler, Goldstein & Fox, P.L.L.C.

(57) ABSTRACT

The present invention provides a photometric reference member comprising PTFE and glass. The member exhibits an absorbance change of less than 0.0001 absorbance units per degree C. over a range of temperatures, preferably from about 20° C. to about 40° C., and over wavelengths from about 600 nm to about 1650 nm, preferably about 600 nm to about 1050 nm. The invention also pertains to methods of using the photometric reference member to correct for temperature variations or drift in absorbance measurements.

17 Claims, 11 Drawing Sheets

DEVICE FOR REFERENCE MEASUREMENT AND PHOTOMETRIC CORRECTION IN NON-INVASIVE GLUCOSE MEASUREMENT USING NEAR INFRARED SPECTROSCOPY

CROSS REFERENCE TO RELATED APPLICATIONS

This application claims the benefit of U.S. Provisional Application No. 60/349,361 filed Jan. 22, 2002.

The present invention relates to a device for performing photometric reference measurements. More specifically, the present invention relates to a device for performing photometric reference measurements and corrections in near infrared spectroscopy.

BACKGROUND OF THE INVENTION

Absorption spectroscopy is a well known analytical technique used to determined the concentration of one or more substances in a sample. In most cases, absorption spectroscopy is performed in a device such as spectrophotometer that comprises in its most basic form, a light source, a sample holder and a detector. Light produced from the light source travels through the sample holder to a detector which measures the amount of light reaching it. In the absence of a sample, light from the source passes unobstructed to the detector. In the presence of a sample, light produced by the light source must pass through the sample before reaching the detector. Prior to interacting with a sample, light produced from a source is usually termed incident light, whereas light that is transmitted through the sample to the detector is called transmitted light. Incident light and transmitted light may differ for example in intensity, wavelength or both. When incident light strikes a sample composition, a portion of the incident light may be reflected, scattered or absorbed by components of the sample. These changes account for the differences between the incident light and transmitted light.

For a non-scattering sample, absorbance of the sample is proportional to the log of amount of incident light illuminating a sample divided by the amount of light transmitted through the sample. The incident light can be measured in a single-beam spectrophotometer by measuring the amount of light reaching the detector with no sample in the chamber. When the sample chamber does not contain a sample, the incident light is often referred to as the reference beam. The incident light for a non-scattering sample is usually less than the amount of light required to saturate the detector, i.e., when the detector has achieved its maximum linear response to changes in light intensity. In order for light to be transmitted through a highly light scattering sample, the intensity of the incident light must be significantly higher than the amount of light required to saturate the detector. In such a case, it is difficult to determine the true intensity of the incident light.

One method of compensating for detector saturation is to use a smaller integration time for the reference measurement, that is the time that the detector remains exposed to the light before the actual signal is collected. However, the use of different integration times for the sample measurements and the reference measurements can lead to error in analyte determinations. Further, when different integration times are used for sample measurements, and reference measurements, the log of the ratio of the sample integration time to reference integration time, must be added to the absorbance value. In such a case, the absorbance of a light-scattering sample may not necessarily be indicative of the true absorbance of the sample.

A second method of compensating for detector saturation is to attenuate the reference beam with a filter or photometric reference member. A photometric reference member or filter may be used to reduce the intensity of the incident light reaching a detector. The photometric reference member may comprise a light-scattering substance, or a neutral density filter. In cases where temperature variations may exist between samples and the analyte being assayed is very low, the absorbance of the photometric reference member should be resistant to temperature changes and the noise level of the spectrophotometer should be very low. For example, for the non-invasive measurement of glucose in a finger, any fluctuation in the contribution of absorbance from the photometric reference member as a result of temperature fluctuations, could affect the accuracy of predicted glucose concentrations.

WO 01/15596 discloses an artificial member which mimics the absorbance spectrum of a body part and includes the spectral components of blood. The application discloses an artificial member that comprises a material which provides a scattering effect similar to tissue such as the skin or a digit, for example, Teflon-PTFE with 25% glass fibers. However, a drawback to the artificial member described in the application is that material comprising 75% PTFE and 25% glass fiber does not exhibit absorbance-related temperature resistance over wavelength ranges that are often used in analytical spectroscopy procedures.

U.S. Pat. Nos. 6,015,610 and 5,596,450 disclose a thin, moldable, flexible and highly reflective material to provide diffuse light. The patents teach the use of expanded polytetrafluoroethylene (PTFE) comprising a microstructure of polymeric nodes and fibrils. A drawback of the materials disclosed in these patents is that PTFE by itself does not exhibit absorbance-related temperature resistance over wavelength ranges used in many analytical spectroscopy procedures.

There is a need in the art for a photometric reference member whose absorbance is resistant to temperature changes. Further, there is a need in the art for a photometric reference member whose absorbance is resistant to temperature changes and that is highly light scattering so that any slight change in the positioning of the photometric reference member within an analytical device does not substantially affect the amount of diffuse light transmitted to the detector.

It is an object of the present invention to overcome disadvantages of the prior art.

The above object is met by a combination of the features of the main claims. The sub claims disclose further advantageous embodiments of the invention.

SUMMARY OF THE INVENTION

The present invention relates to a device for performing photometric reference measurements. More specifically, the present invention relates to a device for performing photometric reference measurements and corrections in near infrared spectroscopy.

According to an aspect of the present invention, there is provided a photometric reference member comprising PTFE and glass, wherein the member exhibits an absorbance change of less than 0.0002 absorbance units per degree C. from about 20° C. to about 40° C. and over a wavelength range from about 600 nm to about 1650 nm, preferably about 600 nm to about 1050 nm.

Also according to the present invention, there is provided a photometric reference member as defined above comprising between about 85% and about 95% (w/w) PTFE and between about 5% and about 15% (w/w) glass fiber. In an embodiment, which is not meant to be considered limiting in any manner, the photometric reference member comprises about 85% (w/w) PTFE and 15% (w/w) glass fiber. In another embodiment contemplated by the present invention, the photometric reference member comprises about 95% (w/w) PTFE and 5% (w/w) glass fiber. Further, the photometric reference member may be molded in any shape desired, for example, but without wishing to be limiting, a sphere, cylinder, cube, rectangular block or body part. Further, the body part may comprise a human body part, for example but not wishing to be limiting a human body part, such as, but not limited to a finger, toe, a portion of an arm or leg, and earlobe. Also, the photometric reference member of the present invention may be solid or it may comprise a cavity.

Also according to the present invention, there is provided the use of the photometric reference member as defined above for reducing the amount of light falling on a detector, for example, but not wishing to be limiting, the detector of a spectroscopic instrument.

Further, according to the present invention, there is provided the use of the photometric reference member as defined above comprising a) measuring a first light intensity value for light transmitted through the photometric reference member in the absence of a sample, b) measuring a second light intensity value for light transmitted through a sample in the absence of the photometric reference member, and c) calculating the absorbance of the sample as the log of the intensity of the light transmitted though the photometric reference member and falling on a detector divided by the intensity of the light passing through the sample and falling on the detector.

Also according to the present invention, there is provided a spectroscopic instrument comprising one or more photometric reference members as defined above.

Also according to the present invention there is provided a method of correcting absorbance measurements comprising the steps of:

a) obtaining one or more of the photometric reference members as defined above, and measuring an initial absorbance value for each of the one or more photometric reference members using an instrument;

b) performing one or more sample absorbance measurements using said instrument;

c) measuring a final absorbance for each of the one or more photometric reference members using said instrument, and;

d) calculating a linear regression equation for the absorbance measurements obtained with the one or more photometric reference members and calculating a linear regression equation defined by a slope and a y-intercept, and;

e) correcting the absorbance of the one or more samples according to the equation:

Corrected absorbance=(measured absorbance−y-intercept)/slope

Preferably, the one or more photometric reference members comprise at least 4 photometric reference members. More preferably, the 4 or more photometric reference members exhibit a range of absorbances which encompasses the range of absorbances values for the samples to be measured. The photometric reference members may comprise different size cavities and the size of the cavities may be varied among a series of photometric reference members of constant size, shape and composition to provide a series of photometric reference members which are capable of absorbing different amount of light.

The present invention also provides a photometric reference member comprising between about 85% (w/w) and about 95% (w/w) PTFE and between about 5% (w/w) and about 15% (w/w) glass fiber, wherein said member is capable of exhibiting a change of less than 0.0002 absorbance units per degree C. from about 20° C. to about 40° C. and over wavelengths from about 600 nm to about 1650 nm. Preferably, the change in absorbance is of less than 0.0001 absorbance units per degree C. from about 20° C. to about 40° C., or from about 25° C. to about 35° C., and over wavelengths from about 600 nm to about 1650 nm, or form about 600 nm to about 1050 nm.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 11A shows a solid photometric reference member and FIG. 11B shows a hollow photometric reference member.

DESCRIPTION OF PREFERRED EMBODIMENT

The present invention relates to a device for performing photometric reference measurements. More specifically, the present invention relates to a device for performing photometric reference measurements and corrections in near infrared spectroscopy.

The following description is of a preferred embodiment by way of example only and without limitation to the combination of features necessary for carrying the invention into effect.

According to an aspect of an embodiment of the present invention there is provided a photometric reference member comprising PTFE and glass. The member exhibits an absorbance change of less than 0.0002 absorbance units, and preferably, 0.0001 absorbance units per degree C. over a range of temperatures, for example, but not limited to from about 20° C. to about 40° C., or from about 25° C. to about 35° C., and over a wavelength range from about 600 nm to about 1650 nm, preferably about 600 nm to about 1050 nm.

By the term "photometric reference member", it is meant an element or member comprised of one or more materials that is capable of transmitting a fraction of incident light directed thereupon. The remaining fraction of the incident light may be absorbed, scattered, reflected, or any combination thereof. Preferably, the photometric reference member is highly light scattering. In this manner the photometric reference member is capable of reducing or attenuating the light intensity from a source. Preferably, the photometric reference member is capable of reducing or attenuating the light intensity by substantially the same amount for all wavelengths transmitted through the member.

The photometric reference member of the present invention may be characterized as comprising one or more of a range of optical densities. The optical density of the photometric reference member may be calculated as the logarithm of the intensity of the incident light falling on an object divided by the intensity of the light transmitted through the object. For example, but not wishing to be considered limiting in any manner, a photometric reference member comprising an optical density of 3 transmits 1/1000th of the incident light falling thereon.

The photometric reference member of the present invention is considered to be temperature resistant, meaning that the absorbance of the member does not change appreciably as a function of temperature. Preferably, the photometric reference member exhibits an absorbance change of less than about 0.0002 absorbance units, and more preferably, less than about 0.0001 absorbance units from about 600 nm to about 1650 nm over a range of temperatures, preferably from about 20° C. to about 40° C. More preferably, the photometric reference member exhibits an absorbance change of less than about 0.0001 absorbance units from about 600 nm to about 1050 nm over a temperature range of about 20° C. to about 40° C.

The photometric reference member preferably comprises PTFE and glass. In an aspect of an embodiment of the present invention, the photometric reference member comprises from about 95% (w/w) to about 85% (w/w) PTFE and from about 5% (w/w) to about 15% (w/w) glass fiber. While the photometric reference member preferably comprises PTFE and glass, other derivatives or variants of PTFE and glass known in the art may be employed in the photometric reference member of the present invention.

In an aspect of the present invention, which is not meant to be limiting in any manner, the photometric reference member comprises about 85% (w/w) PTFE and about 15% (w/w) glass fiber. Also provided, and is not to be considered limiting, is a photometric reference member that comprises about 95% (w/w) PTFE and about 5% (w/w) glass fiber.

Referring now to FIGS. 1 to 8 there are shown graphic results depicting the absorbance change per degree C. (y-axis) and the wavelength in nanometers (x-axis), for photometric reference members comprising different materials over a range of wavelengths in the near infrared and adjacent visible spectrum, using a silicon detector. FIGS. 1–6 pertain to prior art photometric reference members, while the data of FIGS. 7 and 8 pertain to the photometric reference members of the present invention.

Figure 1:
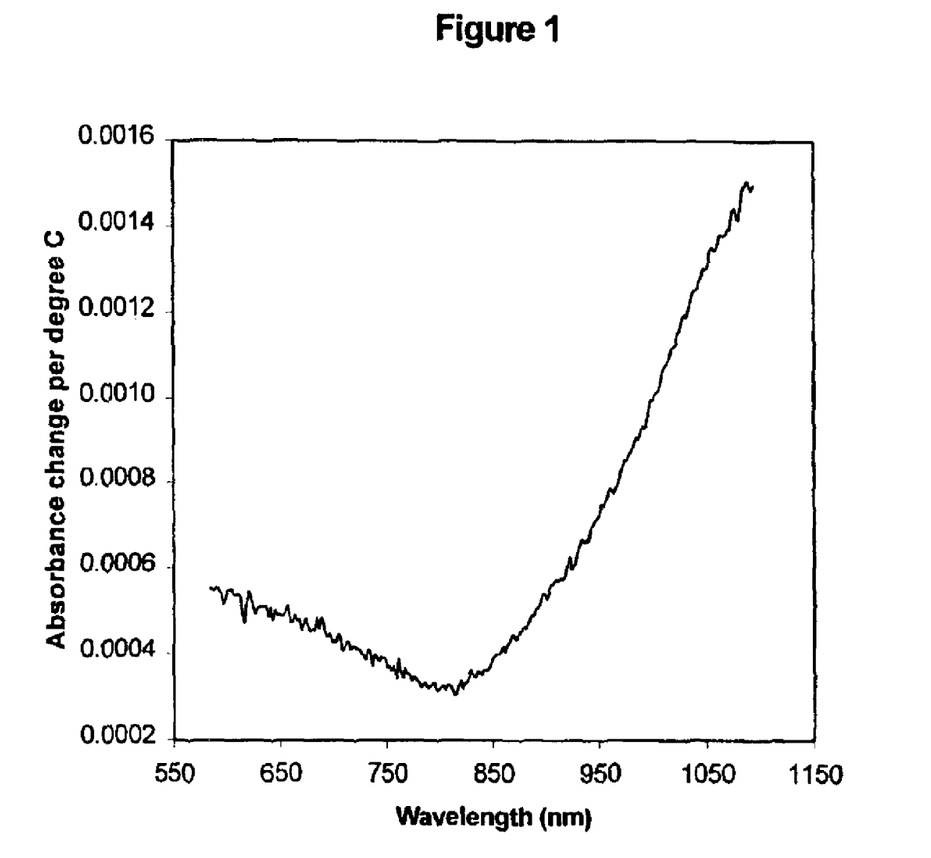
FIG. 1 shows a graphic representation of the absorbance change per degree C. (y-axis) versus the wavelength in nanometers (x-axis) for polytetrafluoroethylene (PTFE), using a silicon detector.

FIG. 1 shows results depicting the temperature resistance of a photometric reference member comprising PTFE. The results shown in FIG. 1 suggest that photometric reference members comprising PTFE exhibit relatively large changes in absorbance per degree C. over a wavelength range from 600 nm to 1050 nm.

Figure 2:
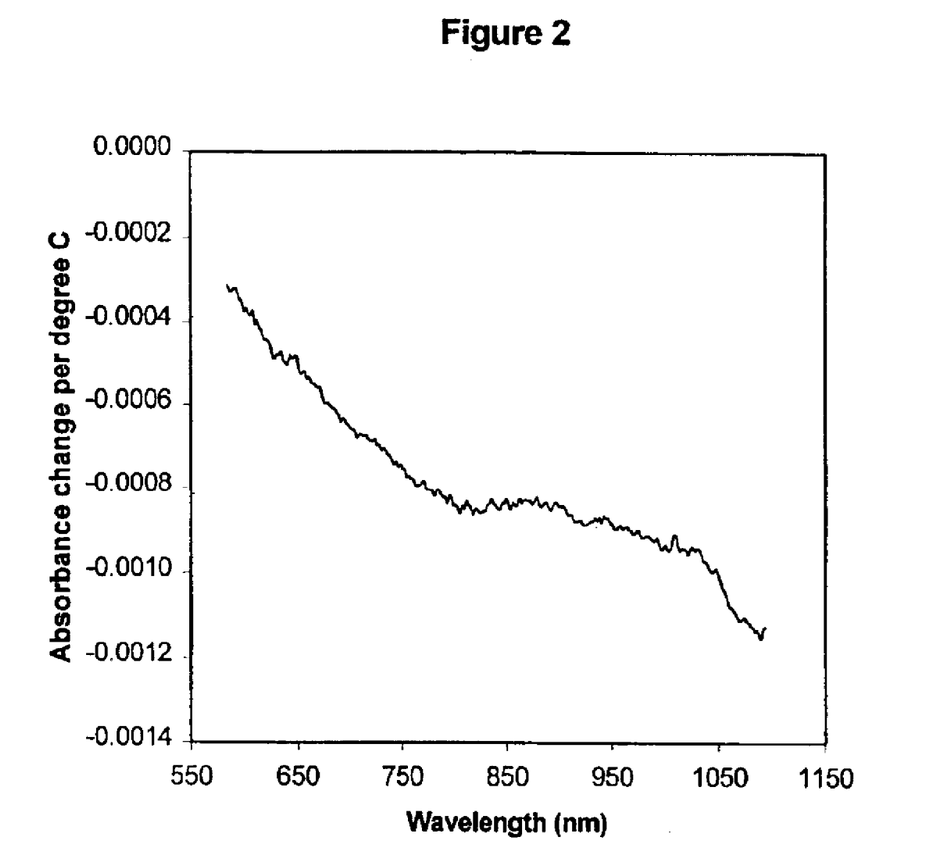
FIG. 2 shows a graphic representation of the absorbance change per degree C. (y-axis) versus the wavelength in nanometers (x-axis) for nylon (Zytel® from DuPont), using a silicon detector.

FIG. 2 shows results depicting the temperature resistance of a photometric reference member comprising nylon (Zytel® from Dupont). The results shown in FIG. 2 suggest that photometric reference members comprising Zytel® exhibit relatively large changes in absorbance per degree C. over a wavelength range from 600 nm to 1050 nm.

Figure 3:
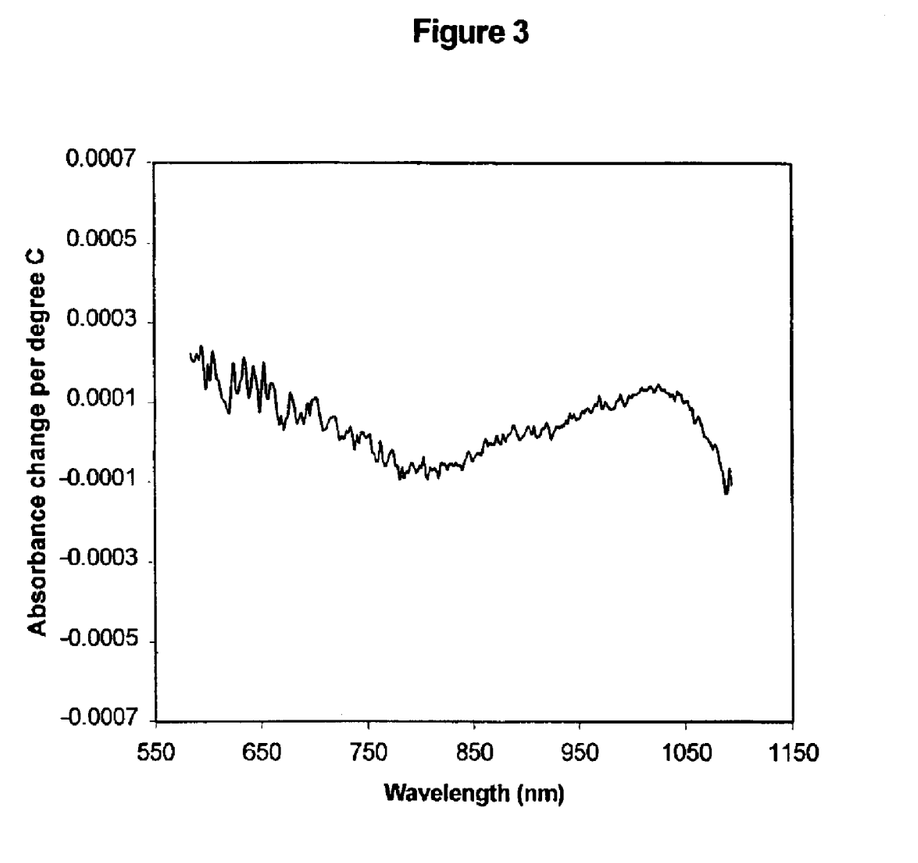
FIG. 3 shows a graphic representation of the absorbance change per degree C. (y-axis) versus the wavelength in nanometers (x-axis) for a combination of PTFE and nylon (Zytel), using a silicon detector.

In FIG. 3 results depicting the temperature resistance of a second light intensity photometric reference member comprising a sandwich combination of PTFE and nylon (Zytel®) are shown. The results shown in FIG. 3 suggest that these photometric reference members exhibit relatively large changes in absorbance per degree C. over a wavelength range from 600 nm to 1050 nm.

Figure 4:
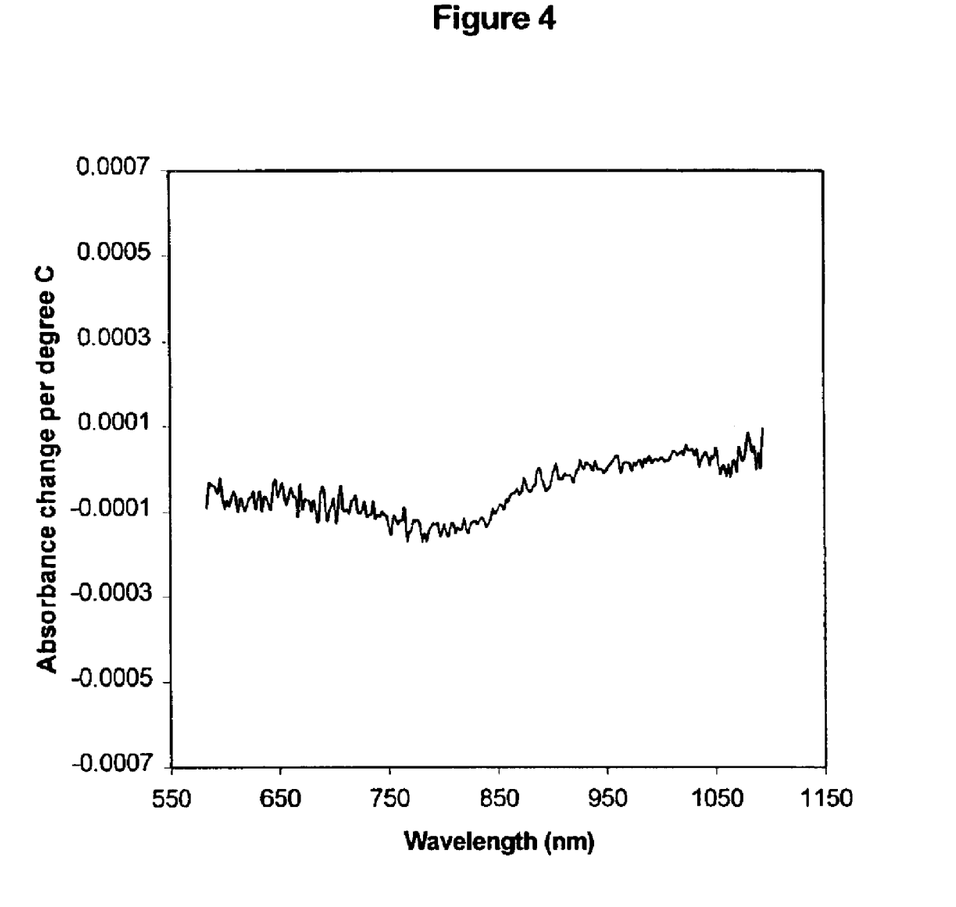
FIG. 4 shows a graphic representation of the absorbance change per degree C. (y-axis) versus the wavelength in nanometers (x-axis) for glass ceramic (Macor® from Corning), using a silicon detector.

FIG. 4 shows results depicting the temperature resistance of a photometric reference member comprising ceramic glass (Macor® from Corning). The results shown in FIG. 4 suggest that photometric reference members comprising ceramic glass exhibit relatively large changes in absorbance per degree C. over a wavelength range from 600 nm to 1050 nm.

Figure 5:
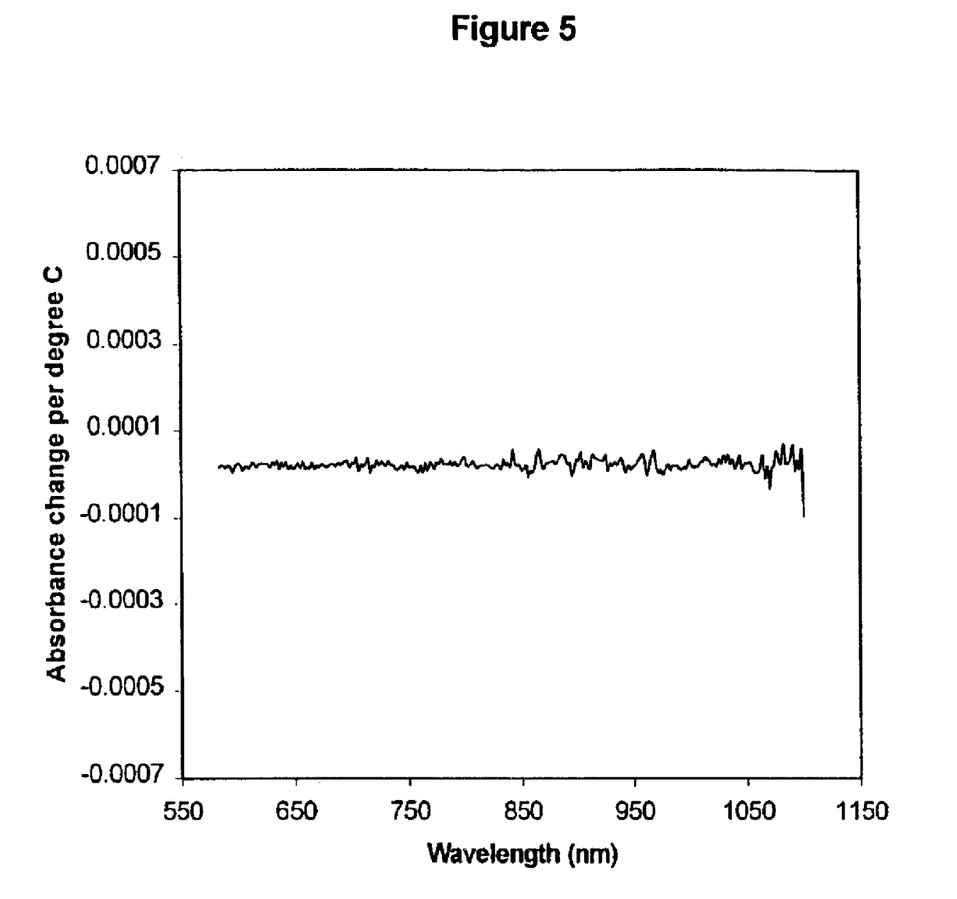
FIG. 5 shows a graphic representation of the absorbance change per degree C. (y-axis) versus the wavelength in nanometers (x-axis) for a 2-OD neutral density filter, using a silicon detector.

With reference to FIG. 5, there are shown results depicting the temperature resistance of a 2× OD neutral density filter. The results provided in FIG. 5 suggest that a 2× OD optical density filter exhibits reduced change in absorbance per degree C. over a wavelength range from about 600 nm to about 1050 nm.

Figure 6:
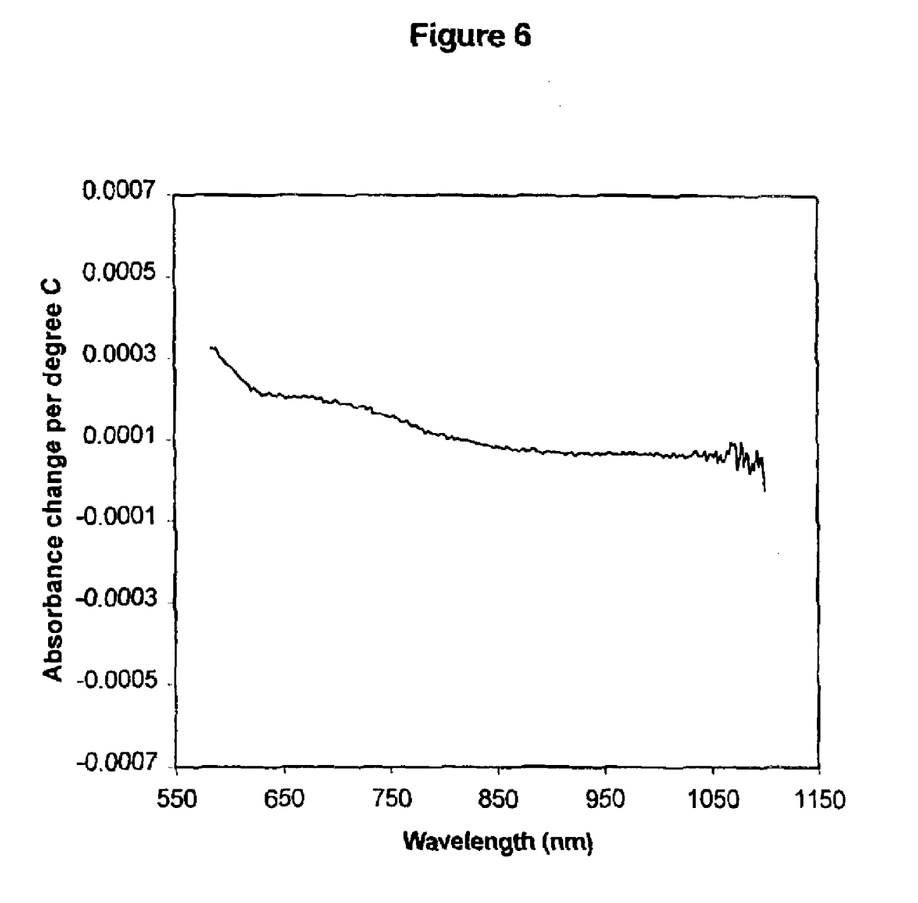
FIG. 6 shows a graphic representation of the absorbance change per degree C. (y-axis) versus the wavelength in nanometers (x-axis) for PTFE containing 25% glass fibers, using a silicon detector.

FIG. 6 shows results depicting the temperature resistance of a photometric reference member comprising 75% (w/w) PTFE and 25% (w/w) glass fibers. The results shown in FIG. 6 indicate that this photometric reference member exhibits a relatively large changes in absorbance per degree C. over a wavelength range from 600 nm to 750 nm and little relatively little change in absorbance from about 750 nm to about 1050 nm under the same conditions.

Figure 7:
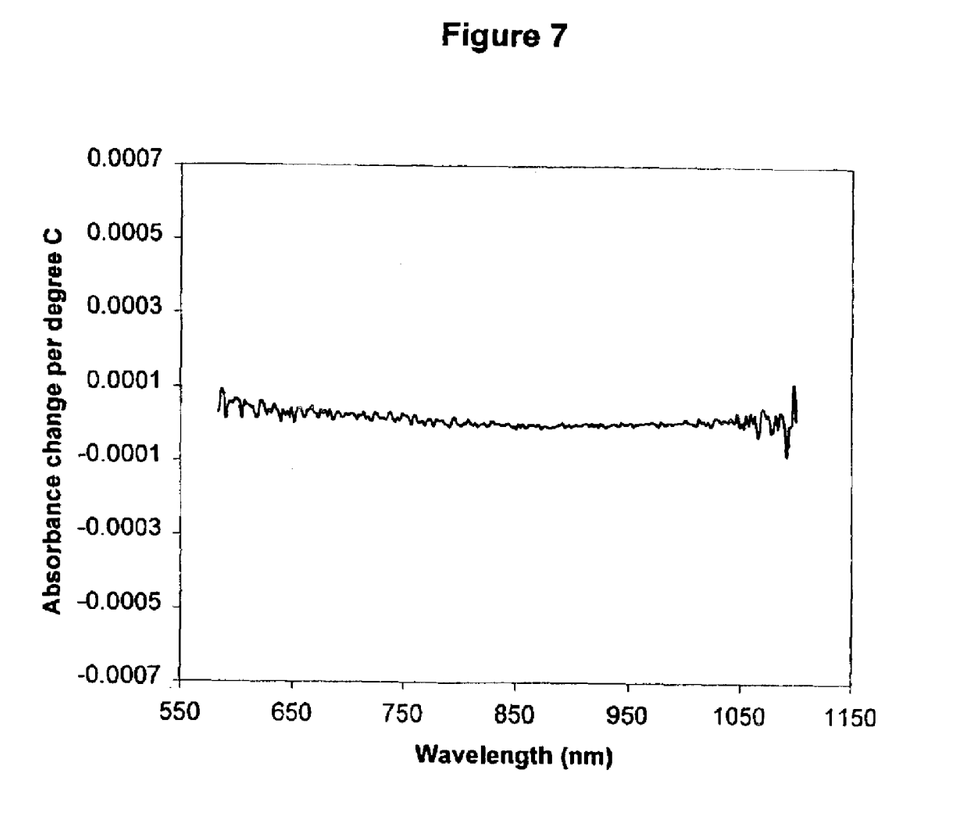
FIG. 7 shows a graphic representation of the absorbance change per degree C. (y-axis) versus the wavelength in nanometers (x-axis) for PTFE containing 15% glass fibers, using a silicon detector.

With reference to FIG. 7 there are shown results depicting the temperature resistance of a photometric reference member comprising about 85% (w/w) PTFE and about 15% (w/w) glass fibers, pertaining to the invention described herein. The results shown in FIG. 7 demonstrate that such a photometric reference member exhibits little change in absorbance per degree C. over a wavelength range from about 600 nm to about 1050 nm.

Figure 8:
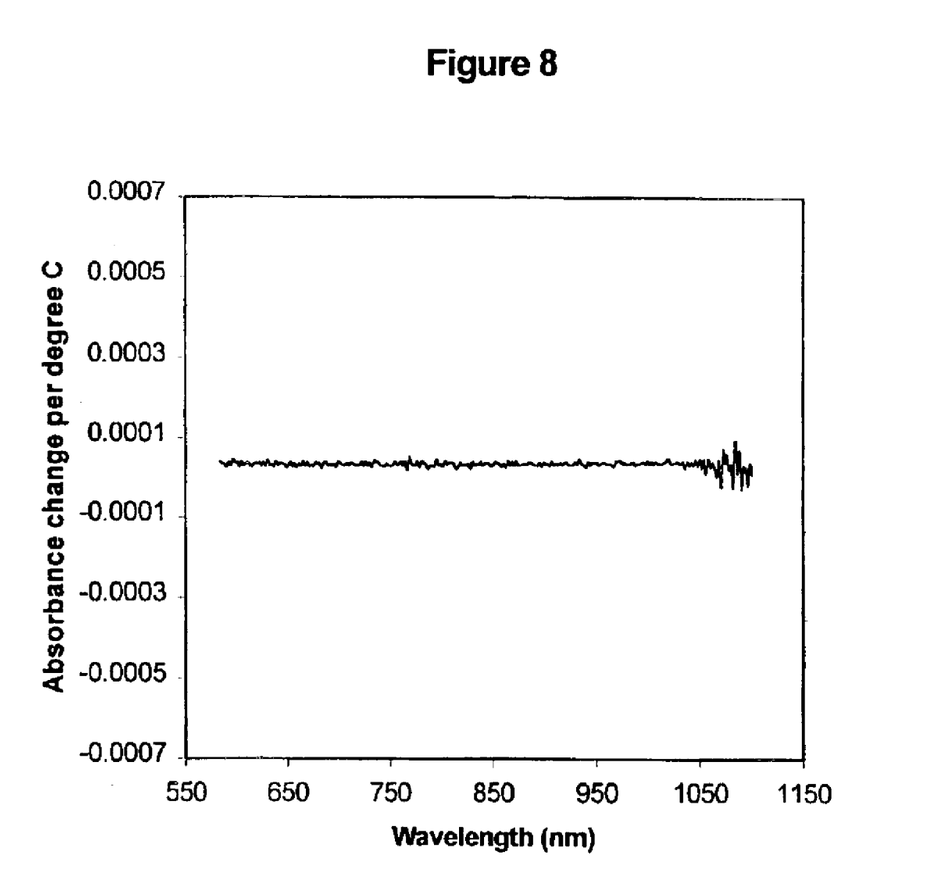
FIG. 8 shows a graphic representation of the absorbance change per degree C. (y-axis) versus the wavelength in nanometers (x-axis) for PTFE containing 5% glass fibers, using a silicon detector.

FIG. 8 shows results depicting the temperature resistance of a light intensity photometric reference member comprising about 95% (w/w) PTFE and about 5% (w/w) glass fibers, pertaining to the invention described herein. The results shown in FIG. 8 suggest that such photometric reference members exhibit little change in absorbance per degree C. over a wavelength range from about 600 nm to about 1050 nm.

The data shown in FIG. 5 demonstrate that a 2x optical density (OD) neutral density filter exhibits reduced variation in absorbance per degree C., or temperature resistance, over a wavelength range of 600 nm to 1050 nm. However, there are several drawbacks associated with the use of neutral density filters as a photometric reference member as described herein. For example, it is well known that neutral density filters do not appreciably scatter incident light. To mimic the scattering of a high density biological sample, a highly light scattering temperature resistant photometric reference member is preferred for making reference measurements and photometric corrections.

As suggested by the results depicted in FIGS. 7 and 8, a photometric reference member according to the present invention that comprises between about 85% (w/w) to about 95% (w/w) PTFE and about 5% (w/w) to about 15% (w/w) glass fiber exhibits relatively little change in absorbance as a function of wavelength from about 650 nm to about 1050 nm over a temperature range from about 20° C. to about 40° C. These results suggest that such photometric reference members may be advantageously employed in spectroscopy conditions where light attenuation is required, for example, but not wishing to be limiting, when attenuation of light intensity is required or when temperature fluctuations among samples are a concern.

Figure 9:
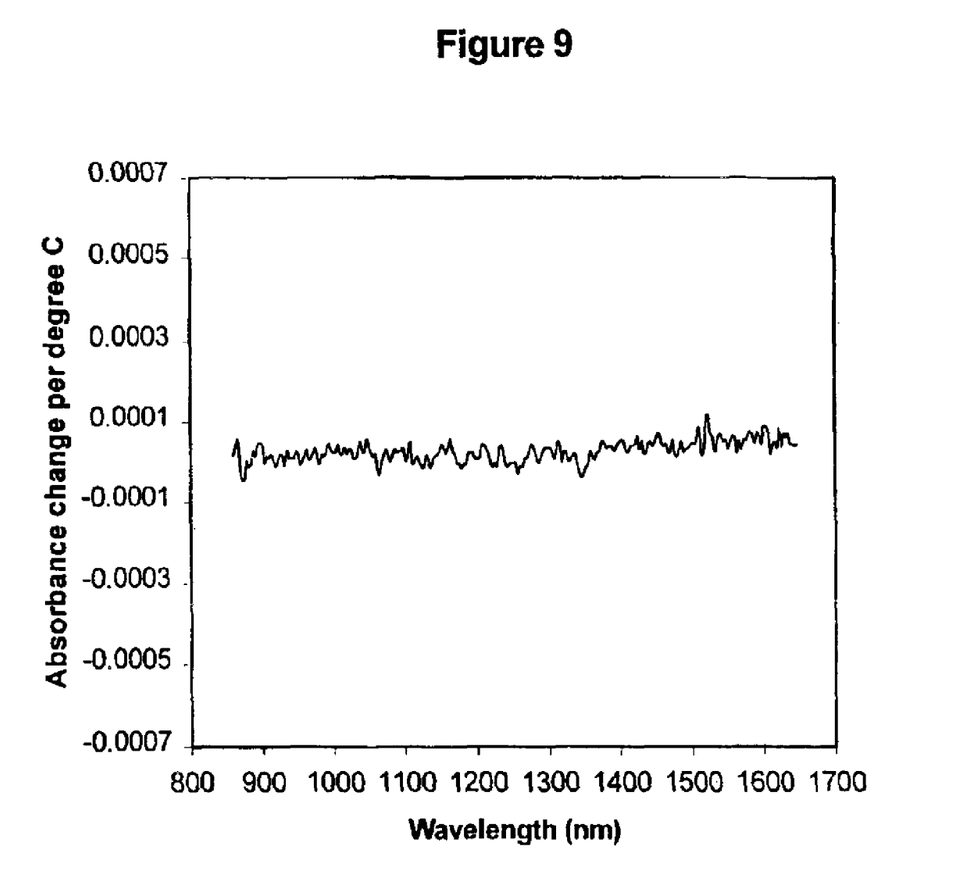
FIG. 9 shows a graphic representation of the absorbance change per degree C. (y-axis) versus the wavelength in nanometers (x-axis) for PTFE containing 5% glass fibers, using an Indium-Gallium-Arsenide detector for longer wavelengths.

Referring now to FIG. 9 there is shown a graphic representation of the absorbance change per degree C. (y-axis) versus wavelength in nanometers (x-axis), for PTFE containing 5% (w/w) glass fibers, using an Indium-Gallium-Arsenide detector. The results shown in FIG. 9 suggest that photometric reference members comprising about 95% (w/w) PTFE and 5% (w/w) glass fibers are temperature resistant from about 20° C. to about 40° C. over a range of wavelengths from about 850 nm to about 1650 nm.

Figure 10:
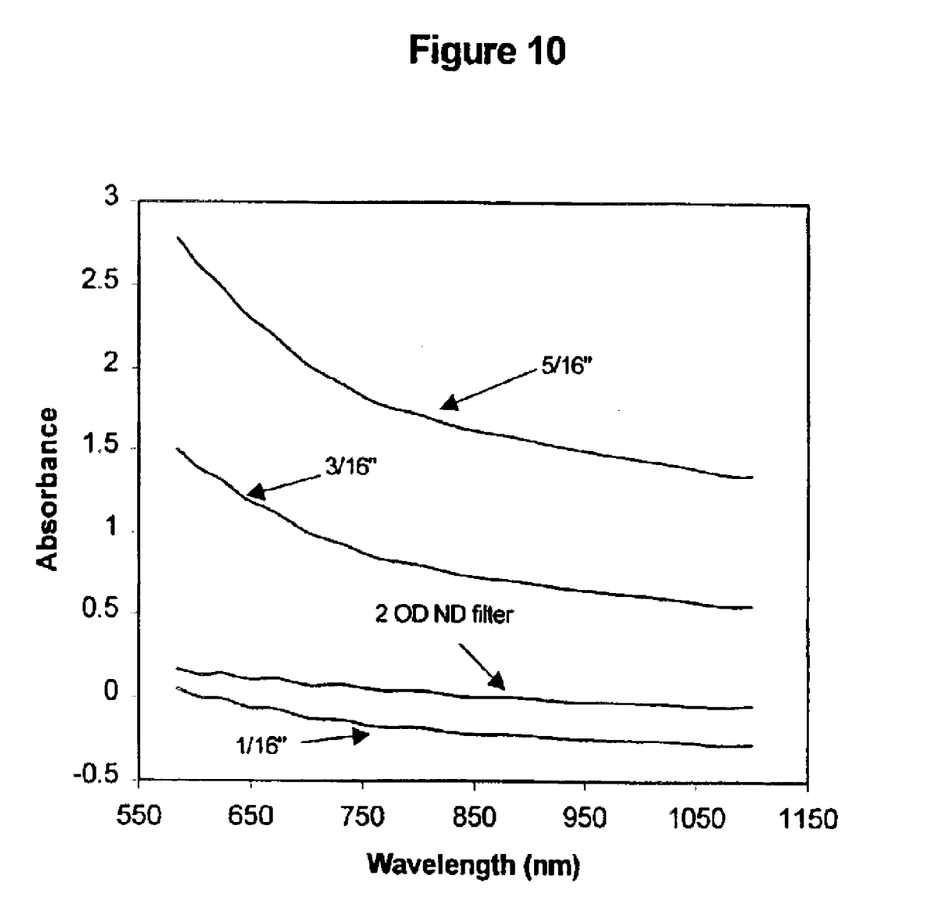
FIG. 10 shows a graphic representation of the absorbance spectra of three different thicknesses of PTFE containing 15% glass fibers and also the absorbance spectra of a 2-OD neutral density filter for comparison, using a silicon detector.

Referring now to FIG. 10, there is shown a graphic representation of the absorbance spectra of three different thicknesses of photometric reference members comprising about 85% (w/w) PTFE and about 15% (w/w) glass fibers using a silicon detector. For comparison, the absorbance spectra of a 2x optical density (OD) neutral density filter is shown for comparison. The results shown in FIG. 10 suggest that the total absorbance of the photometric reference member is related to its thickness. Without wishing to be bound by theory, the absorbance of a photometric reference member of a given composition, is proportional to the path length that the transmitted light travels through the material of the photometric reference member.

Similar photometric reference members of constant shape and volume and composition, but comprising different size cavities, and hence different wall thicknesses, absorb different total amounts of light. The present invention fully contemplates both solid photometric reference members as well as photometric reference members comprising cavities. The photometric reference member of the present invention maybe molded into a specific shape or may be unmolded. Examples of specific shapes contemplated by the present invention include, but are not limited to cylinders, spheres, cubes, rectangular blocks, sheets and the like. Further, the photometric reference member of the present invention may be molded in a shape which is similar to a body part, for example, but not limited to fingers, toes, and earlobes. The photometric reference member of the present invention may also be solid or comprise a cavity.

Figure 11:
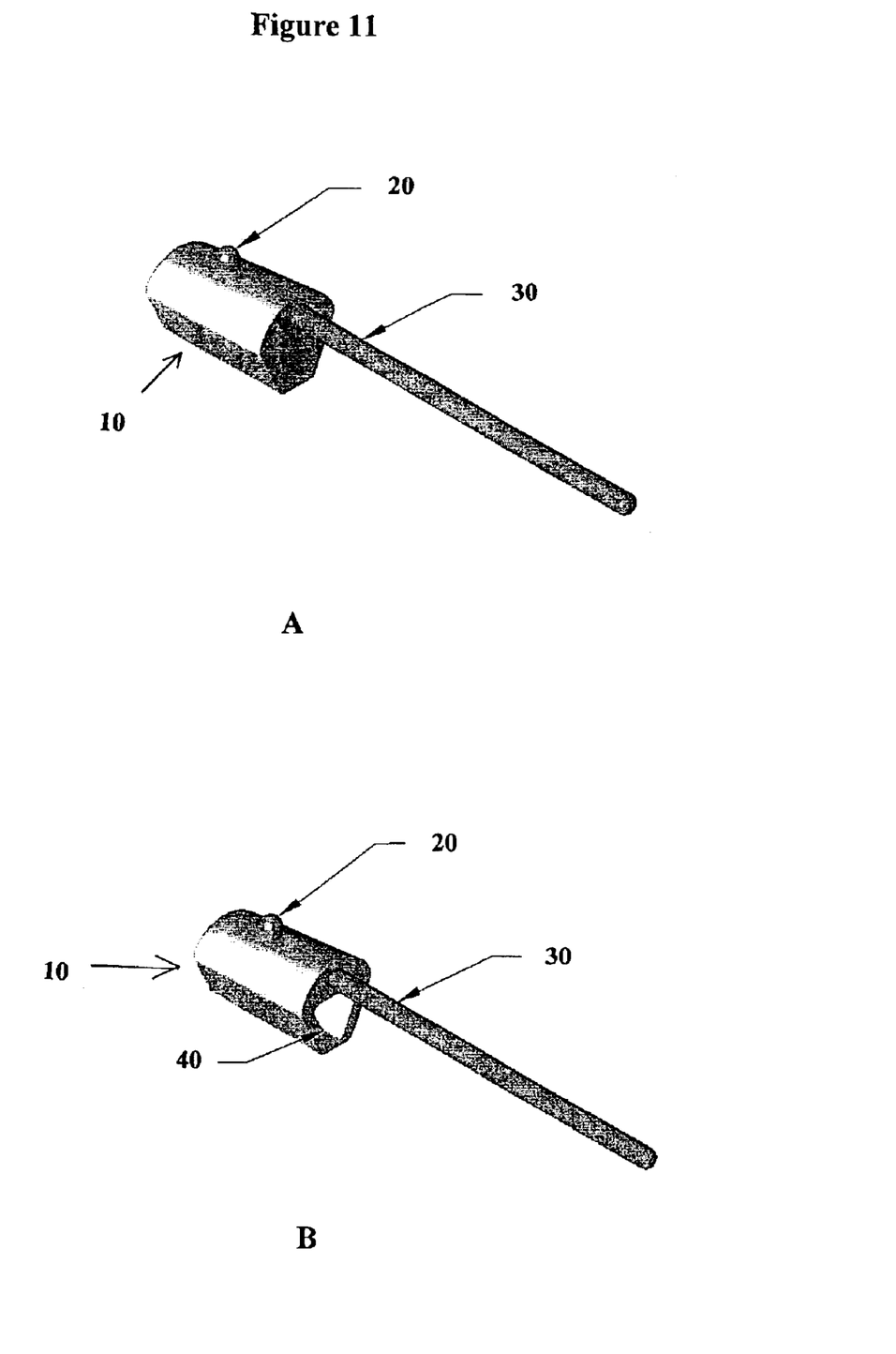
FIG. 11 shows a perspective view of the finger-like photometric reference member used for making photometric correction.

The present invention also contemplates photometric reference members molded into shapes, such as but not limited to a shape similar to a human finger, for example as shown in FIG. 11. The photometric reference member shown in FIG. 11 may be used to reduce the intensity of light reaching a detector or it may be used to make photometric absorbance corrections in a spectroscopic device which accepts a finger, such as the spectrophotometric device described in U.S. Pat. Nos. 5,361,758 and 5,429,128 which are incorporated herein by referecne. In FIG. 11A there is shown a photometric reference member (10) that is solid and further comprises a locking mechanism (20) for example, but not limited to, an interlocking stud, and handle (30), while in FIG. 11B there is shown a similar photometric reference member comprising a cavity (40). Generally, for photometric reference members of a constant volume, shape and composition, a photometric reference member with a larger cavity will have thinner walls than a photometric reference member with a smaller cavity. According to the results depicted in FIG. 10 a photometric reference member with a larger cavity will exhibit a lower total absorbance compared to an photometric reference member with a smaller cavity. Thus, the cavity size may be varied in a series of photometric reference members of constant volume, shape and composition to produce photometric reference members which exhibit different absorbances.

The photometric reference member of the present invention may be mechanically or automatically inserted into the incident light path during a reference measurement, preferably with no sample present. The absorbance of the sample is usually determined when the photometric reference member is not present in the incident beam, as would be evident to someone of skill in the art. However, in dual beam instruments, the photometric reference member maybe retained for comparative reference measurements.

The photometric reference member of the present invention may be employed in a spectrophotometer or other analyte determination device. Specifically, but not wishing to be limiting, the photometric reference member of the present invention may be, but is not limited to being, employed in any device wherein the intensity of a light source is to be diminished for a reference measurement, for example during reference measurement of the incident light intensity of a highly light scattering sample.

The present invention also pertains to a method for photometric correction of measured absorbances, for example, but not wishing to be limiting, when there exists temperature variation between samples or when drift is suspected. However, photometric detection may be applied for other reasons, including instrument drift, noise and other factors that contribute to background.

The following example is meant to be exemplary and is not to be construed as limiting in any manner. As would be evident to someone of skill in the art, the method may be modified without departing from the scope of the invention as disclosed herein.

In an aspect of an embodiment of the present invention there is provided a method of photometric correction of absorbances obtained via non-invasive measurement of glucose, for example, but not to be considered limiting as taught in U.S. Pat. No. 5,361,758 (which is herein incorporated by reference) and employing a finger receptor, for example but not wishing to be limiting, as described in U.S. Pat. No. 5,429,128. However, other receptors may be used for measurements of any body part, for example, earlobe, toe, a portion of an arm, a portion of a leg. The photometric reference member may be used for in vivo or in vitro measurements as required.

The method of photometric detection generally comprises taking a series of absorption measurements, for example, using four or more photometric reference members. Preferably, each photometric reference member is molded in a shape which is complementary to the shape of the receptor of the spectroscopic measuring device.

Immediately before patient finger measurements are collected for development of the glucose calibration algorithm, one or more finger-shaped photometric reference members of the present invention, for example, one or more reference members made of PTFE containing 5% (w/w) glass fiber, are tested and the absorbance measurements saved. For example a series of 4 reference members may be tested, where the 4 reference absorbance measurements would encompass the absorbance range obtained from live finger measurements. However, it is to be understood that fewer than 4, or more than 4 measurements may be contained. It is preferred that these measurements are made at the beginning and at the end of each day patient finger measurements are collected. However, measurements using the photometric reference member of the present invention may be made before and after each sample measurement, or as required. Linear regression equations maybe calculated for the reference absorbance measurements over the wavelength range scanned, for example, but not limited to as shown in FIG. 9 and by plotting the initial absorbance on the x-axis, and the later measurement on the y-axis. The linear regression equation for each wavelength is characterized by a slope and a y-intercept. The basis of the correction for an absorbance measurement may be performed using the equation:

Corrected absorbance=(measured absorbance−y-intercept)/slope.

As will be evident to someone of skill in the art, the method of photometric correction is not restricted to non-invasive glucose measurement or devices for non-invasive glucose measurement, but can be used in any spectrosopic assay or device for photometric correction, and for the analysis of any compound within a sample.

The above description is not intended to limit the claimed invention in any manner, Furthermore, the discussed combination of features might not be absolutely necessary for the inventive solution. All references are herein incorporated by reference. The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A photometric reference member comprising between about 85% (w/w) and about 95% (w/w) PTFE and between about 5% (w/w) and about 15% (w/w) glass fiber.

2. The photometric reference member of claim 1, wherein said member is capable of exhibiting a change of less than 0.0002 absorbance units per degree C. from about 20° C. to about 40° C. and over wavelengths from about 600 nm to about 1650 nm.

3. The photometric reference member of claim 1 comprising about 85% (w/w) PTFE and 15% (w/w) glass fiber.

4. The photometric reference member of claim 1 comprising about 95% (w/w) PTFE and about 5% (w/w) glass fiber.

5. The photometric reference member of claim 1, said photometric reference member moulded in a shape selected from the group consisting of sphere, cylinder, cube, rectangular block or body part.

6. The photometric reference member of claim 5, wherein said shape is a body part.

7. The photometric reference member of claim 6, wherein said body part is a human body part.

8. The photometric reference member of claim 7, wherein said human body part is selected from the group consisting of a finger, a toe, a portion of an arm, a portion of a leg, and an earlobe.

9. The photometric reference member of claim 8, wherein said human body part is said finger.

10. The photometric reference member of claim 5, wherein said photometric reference member is solid or comprises a cavity.

11. A method for reducing the amount of light falling on a detector comprising the steps of:
    measuring a first light intensity value for light passing through said photometric reference member defined in claim 1 in the absence of a sample,
    measuring a second light intensity value for light passing through a sample in the absence of said photometric reference member, and
    calculating the absorbance of the sample as the log of the intensity of the light passing though the photometric reference member and falling on a detector divided by the intensity of the light passing through the sample and falling on the detector.

12. A spectroscopic instrument comprising one or more photometric reference members as defined by claim 1.

13. A method of correcting absorbance measurements comprising the steps of
    a) obtaining one or more of the photometric reference members of claim 1 and measuring an initial absorbance of said one or more photometric reference members using an instrument;
    b) performing one or more sample absorbance measurements on said instrument;
    c) measuring a final absorbance for said one or more photometric reference members on said instrument, and;
    d) calculating a linear regression equation for thereby providing a linear equation defined by a slope and a y-intercept, and;
    e) correcting the absorbance of said sample according to equation:

Corrected absorbance=(measured absorbance−y-intercept)/slope.

14. The method of claim 13, wherein said one or more photometric reference members comprise at least 4 photometric reference members.

15. The method of claim 14, wherein of said at least 4 photometric reference members, at least one of said photometric reference members absorbs less light than the lowest absorbing sample and at least one of said photometric reference members absorbs more light than the highest absorbing sample.

16. The method of claim 15, wherein said photometric reference members comprise different size cavities.

17. The reference member of claim 1 wherein said member is capable of exhibiting a change of less than 0.0001 absorbance units per degree C. from about 25° C. to about 35° C. and over wavelengths from about 600 nm to about 1050 nm.

* * * * *